US011662496B2

(12) United States Patent
Cabella et al.

(10) Patent No.: US 11,662,496 B2
(45) Date of Patent: May 30, 2023

(54) THROUGH TUBING ACOUSTIC MEASUREMENTS

(71) Applicant: Halliburton Energy Services, Inc., Houston, TX (US)

(72) Inventors: Brenno Caetano Troca Cabella, Rio de Janeiro (BR); Ruijia Wang, Singapore (SG); Chung Chang, Houston, TX (US); Qingtao Sun, Spring, TX (US); Yao Ge, Singapore (SG); Xiang Wu, Singapore (SG); Pablo Vieira Rego, Rio de Janeiro (BR); Marco Aurelio Luzio, Rio de Janeiro (BR); João Vicente Gonçalves Rocha, Petrópolis (BR)

(73) Assignee: Halliburton Energy Services, Inc., Houston, TX (US)

( * ) Notice: Subject to any disclaimer, the term of this patent is extended or adjusted under 35 U.S.C. 154(b) by 172 days.

(21) Appl. No.: 17/327,792

(22) Filed: May 24, 2021

(65) Prior Publication Data
US 2022/0373706 A1 Nov. 24, 2022

(51) Int. Cl.
*G01V 1/50* (2006.01)
*G01N 33/38* (2006.01)
(Continued)

(52) U.S. Cl.
CPC .............. *G01V 1/50* (2013.01); *E21B 47/005* (2020.05); *G01N 33/383* (2013.01); *G01V 1/159* (2013.01);
(Continued)

(58) Field of Classification Search
CPC . G01V 1/50; G01V 1/159; G01V 1/52; G01V 1/40; G01V 2210/1299;
(Continued)

(56) References Cited

U.S. PATENT DOCUMENTS 5,036,496 A     7/1991  Rutledge
6,018,496 A *  1/2000  Stanke .................. E21B 47/005
                                                     181/105
(Continued)

OTHER PUBLICATIONS

Xu, et al., "Acoustic Source Characterization for a Logging While Drilling Tool: Theoretical and Experimental Modeling", Acoustical Society of America, The Journal Acoustical Society of America 144, JASA Express Letters, https://doi.org/10.1121/1.5053105, Sep. 10, 2018, pp. EL 178-EL 184.
(Continued)

*Primary Examiner* — Son T Le
*Assistant Examiner* — Lal C Mang
(74) *Attorney, Agent, or Firm* — Delizio, Peacock, Lewin & Guerra

(57) ABSTRACT

Methods, systems, and program products are disclosed for implementing acoustic logging and determining wellbore material characteristics. In some embodiments, a method may include determining a polar differential signal for each of one or more pairs of azimuthally offset acoustic measurements within a wellbore. A reference azimuth is identified based, at least in part, on comparing the polar differential signals to a modeled bonding differential signal within a target response window. The method further includes determining differences between an acoustic measurement at the reference azimuth and acoustic measurements at one or more other azimuths and determining a wellbore material condition based, at least in part, on the determined differences.

20 Claims, 12 Drawing Sheets

(51) Int. Cl.
    *G01V 1/02*     (2006.01)
    *E21B 47/005*     (2012.01)
    *G06F 30/20*     (2020.01)
    *E21B 47/12*     (2012.01)

(52) U.S. Cl.
    CPC .............. *G06F 30/20* (2020.01); *E21B 47/12* (2013.01); *E21B 2200/20* (2020.05); *G01V 2210/1299* (2013.01); *G01V 2210/1429* (2013.01)

(58) Field of Classification Search
    CPC .......... G01V 2210/1429; E21B 47/005; E21B 47/12; E21B 47/107; E21B 2200/20; G01N 33/383; G06F 30/20
    See application file for complete search history.

(56) References Cited

U.S. PATENT DOCUMENTS

| | | |
|---|---|---|
| 8,755,248 B2 | 6/2014 | Wang |
| 10,067,262 B2 | 9/2018 | Quintero et al. |
| 10,408,037 B2 | 9/2019 | Grisch et al. |
| 10,801,997 B2 | 10/2020 | Zhao et al. |
| 10,858,933 B2 | 12/2020 | Bose et al. |
| 2015/0331134 A1* | 11/2015 | Haldorsen ................ G01V 1/50 367/35 |
| 2020/0033494 A1 | 1/2020 | Pai et al. |
| 2020/0049850 A1* | 2/2020 | Liu .......................... E21B 47/00 |
| 2020/0064505 A1* | 2/2020 | Maxfield .................. G01V 1/48 |
| 2020/0088901 A1 | 3/2020 | Quintero et al. |

OTHER PUBLICATIONS

"GB Application No. 2113539.7 Combined Search and Examination Report", dated Mar. 4, 2022, 9 pages.

Wang, et al., "Understanding Acoustic Methods for Cement Bond Logging", 2016 Acoustical Society of America, 139/5, May 2016, pp. 2407-2416.

* cited by examiner

THROUGH TUBING ACOUSTIC MEASUREMENTS

BACKGROUND

The disclosure generally relates to downhole acoustic measurements and to systems and method for applying polar differential processing to determine material properties such as cement bonding.

Well development, completion, and termination operations often include evaluating wellbore structural features such as the annular cement sheath between a borehole wall and a metallic wellbore casing. Evaluation of the cement sheath in terms of bonding within the borehole and the casing may be helpful in determining quality of well zonal isolation that is important to ensure sufficient downhole pressure seals to prevent leakage of formation fluids from downhole to surface or into adjacent formations. Wellbore structural evaluation may be performed following cementing and/or during the production life of a well and/or before and in preparation for plug and abandonment. For example, cement bond logging (CBL) is a technique in which an acoustic measurement took such as an ultrasonic measurement tool, is utilized to collect acoustic measurement data that may be interpreted to determine bonding integrity particularly between the casing and cement.

Following cementing of a new well and prior to production, the acoustic measurement tool may be deployed such as via wireline into a cased and cemented borehole prior. Such acoustic measurement tools and techniques are relatively effective prior to deployment or otherwise in the absence of additional tubing such as production tubing that diminish acoustic signal transmission. However, withdrawing downhole tubing from a cased borehole to conduct acoustic testing is a large scale and expensive procedure. For plug and abandonment of a well, such as an offshore well for example, extraction of the production tubing to perform CBL measurements to verify the condition of aging cement and cement bonds is a time consuming and expensive procedure.

A completed wellbore typically includes two or more concentrically layered metallic tubulars such as the outer casing and additional inner casings and production strings. The multiple concentric layers present substantial complexity in obtaining sufficiently precise and accurate final results from processing the acoustic signature which incorporates multiple variable factors such as annular thickness and uniformity, material variations, and acoustic signal source variation.

BRIEF DESCRIPTION OF THE DRAWINGS

Embodiments of the disclosure may be better understood by referencing the accompanying drawings.

DESCRIPTION

Figure 1A:
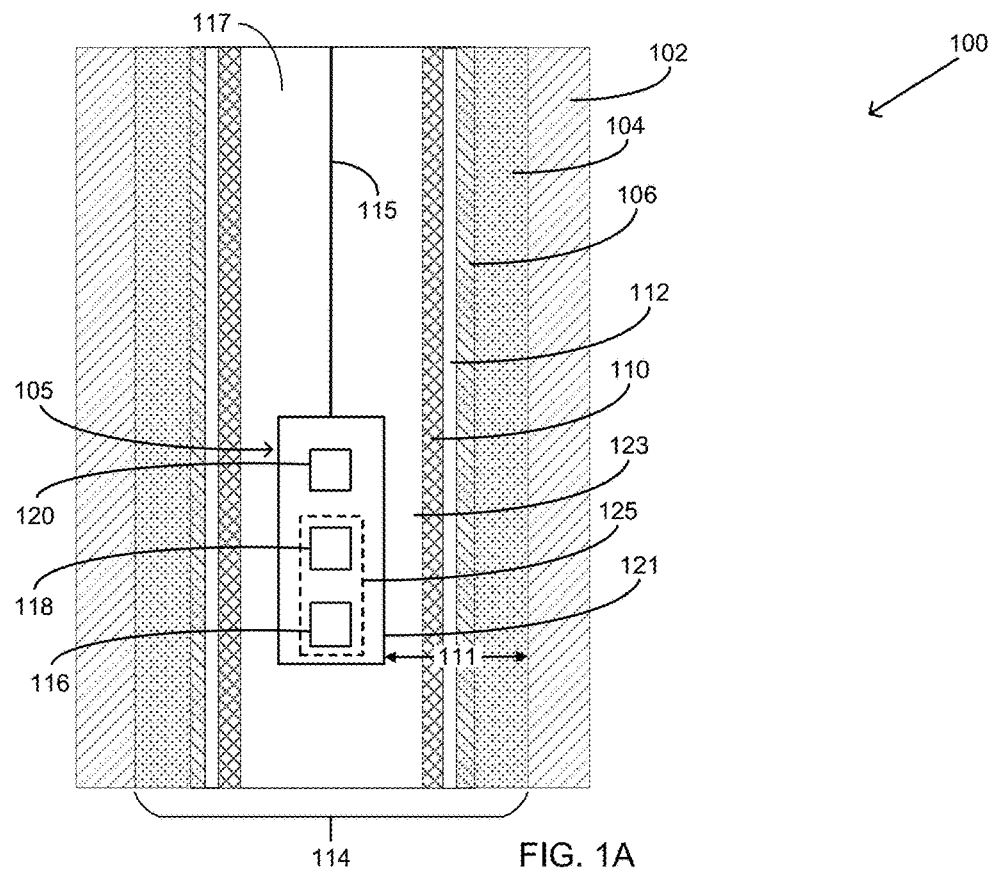
FIG. 1A depicts a side cross-section view of a downhole through tubing cement evaluation (TTCE) system that includes an acoustic logging tool configured in accordance with some embodiments.

The description that follows includes example systems, methods, techniques, and program flows that embody aspects of the disclosure. However, it is understood that this disclosure may be practiced without these specific details. In other instances, well-known instruction instances, protocols, structures and techniques have not been shown in detail in order not to obfuscate the description.

Overview

Embodiments are directed to increasing the measurement sensitivity of through tubing wellbore evaluation such as TTCE and direct high energy acoustic signals at target points such as at or near a casing, a cement layer, and/or a casing/cement interface. In some embodiments, an azimuthally directional acoustic sensor is disposed at an axial location along the length of a wellbore. The wellbore may comprise multiple distinct annular material layers including at least two metallic tubing layers such as a production tubing string within a casing string. The metallic layers may be interleaved between annular fluid layers and an annular cement layer is typically formed outside a casing string between the casing and downhole strata. The acoustic sensor is disposed in an innermost conduit within the wellbore and may comprise a unipolar (i.e., unidirectional) acoustic transmitter and/or acoustic receiver that are configured to measure acoustic response signals (e.g., acoustic echoes) that can be further processed to determine material conditions within the wellbore. The acoustic sensor may collect one or more pairs of azimuthally offset (e.g., 180° azimuthally offset) acoustic measurements at an axial test location along the wellbore.

The pairs of acoustic measurements are processed to determine a polar differential signal for each for each of the pairs. For example, a polar differential signal may comprise a signal resulting from subtracting the amplitude of an acoustic measurement at a first azimuthal angle from the amplitude of an acoustic measurement at a second, azimuthally offset angle. A reference azimuth may be identified or otherwise determined based, at least in part, on comparing the polar differential signals with a modeled differential signal within a target acoustic response window. For cement bonding evaluation, the reference azimuth is identified by comparing the polar differential signals with a modeled differential signal within a cement boundary echo window. The modeled differential signal may be generated from the difference between a bonded acoustic response model and a non-bonded or "free pipe" acoustic response model.

The identified/selected reference azimuth may be utilized to generate a material condition index corresponding to the axial location along the wellbore. In some embodiments, the method may include determining differences between the raw acoustic measurement collected at the reference azimuth and acoustic measurements collected at the other azimuths. A wellbore material condition may be determined based, at least in part, on the determined differences.

Example Illustrations

Figure 1B:
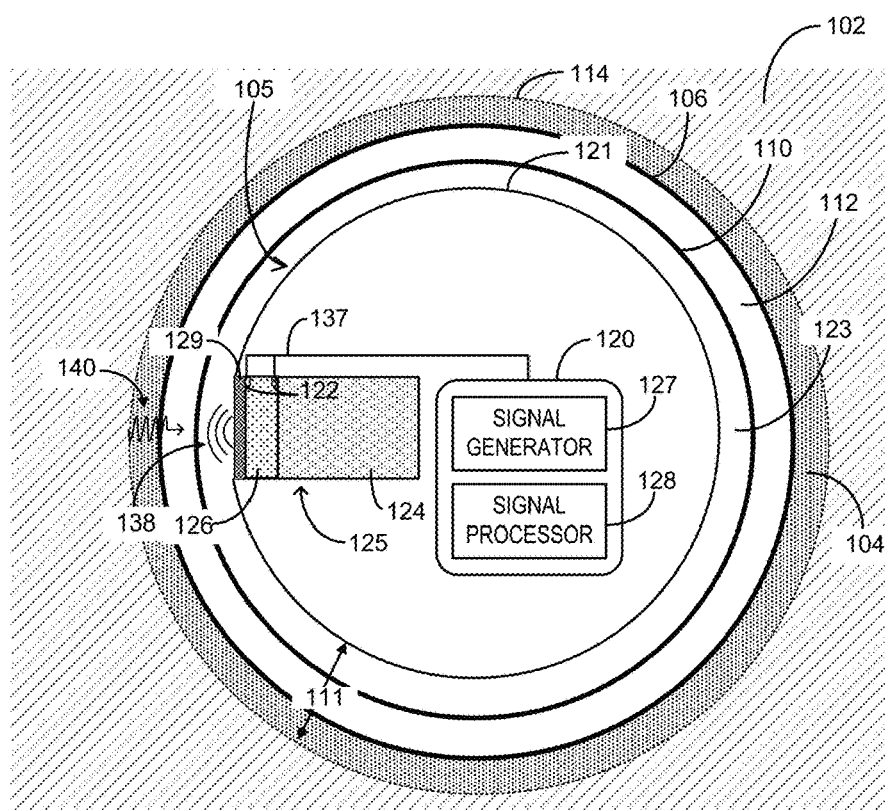
FIG. 1B is an overhead cross-section diagram depicting the acoustic logging tool depicted in FIG. 1A in accordance with some embodiments.

FIG. 1A depicts a side cross-section view of a downhole through tubing cement evaluation (TTCE) apparatus 100 that includes an acoustic logging tool 105 configured in accordance with some embodiments. FIG. 1B is an overhead cross-section diagram depicting TTCE apparatus 100 including acoustic logging tool 105 in accordance with some embodiments. As shown in FIGS. 1A and 1B (collectively, FIG. 1), acoustic logging tool 105 is deployed within a well that is defined by a wellbore 114 in which a production tubing 110 is installed within cement and metallic casing layers. Acoustic logging tool 105 is generally configured to induce acoustic echo responses and process the responses to determine material and structural properties of multiple material layers within wellbore 114. For example, the echo responses may comprise reflected and/or refracted acoustic waves generated when acoustic signals transmitted from acoustic logging tool 105 reflect and/or refract at acoustic impedance boundaries within and between the wellbore layers.

Wellbore 114 is formed within a subsurface strata 102, such as may comprise a hydrocarbon formation in part, by drilling, and is typically filled with liquid and/or slurry substances such as water, reservoir fluids, etc. The outer perimeter of wellbore 114 is sealed from strata 102 by one or more barrier layers. For instance, a casing 106 comprises a metallic tubular member forming an inner liner that seals the interior of wellbore 114. To securely position casing 106 with respect to the inner surface of strata 102, a cement layer 104 is formed between casing 106 and the inner surface of strata 102 that bounds wellbore 114. Production tubing 110 is installed within the cylindrical interior space of casing 106 to form an innermost production conduit 117 and an annular space 112 that typically forms an annular fluid layer between the outer surface of production tubing 110 and the inner surface of casing 106.

Acoustic logging tool 105 includes a tool housing 121 within which an acoustic sensor 125 and a controller 120 are disposed. As shown in FIG. 1A, acoustic sensor 125 comprises an acoustic transmitter 116 and an acoustic receiver 118 within tool housing 121 within which controller 120 is also disposed. Acoustic logging tool 105 is positioned within the innermost production conduit 117 in production tubing 110 with an additional annular fluid layer 123 formed in the annular space between the outer surface of tool housing 121 and the inner surface of production tubing 110. The acoustic sensor components are movably disposed within the fluid and along the length of production conduit 117 via a conveyance means 115 such as a wireline or slickline. In some embodiments, acoustic sensor 125 may be configured with acoustic transmitter 116 and acoustic receiver 118 being individually contained and independently movable components. Alternatively, acoustic sensor 125 may be configured within a contiguous sensor housing such as depicted in FIG. 1 in which both transmitter 116 and receiver 118 are contained in a common tool housing 121.

Acoustic logging tool 105 comprises acoustic source/transmission components and acoustic detection and processing components within acoustic sensor 125. The transmitter and receiver components of acoustic sensor 125 are configured to measure acoustic responses, such as in the form of acoustic echoes, generated from acoustic source signals transmitted from acoustic transmitter 116 to various acoustic response target points within wellbore 114. In the depicted embodiment of FIG. 1B, acoustic sensor 125 comprises a transmitter and/or receiver that are configured as piezoelectric transducers that are electrically, optically, or otherwise communicatively coupled to controller 120. The overhead representation in FIG. 1B of acoustic sensor 125 may represent either a transmitter and/or a receiver, which may be distinct, axially offset components as shown in FIG. 1A.

As shown in FIG. 1B, acoustic sensor 125 includes a transducer comprising a piezoelectric material layer 126 and a pair of electrodes 122 coupled to a front side and a back side of piezoelectric material layer 126. An electrical or optical communication interface 137 provides electrical contact and connectivity between acoustic sensor 125 and controller 120. Acoustic sensor 125 further includes a backing material layer 124 disposed behind piezoelectric material layer 126. Backing material layer 124 comprises acoustic attenuation material such as ultrasonic attenuation material that is compositionally and structurally configured to attenuate acoustic waves emitted from the back side of the primary transducer. Acoustic sensor 125 further includes a protective cover layer 129 coupled to the radially outward front side of the transducer. Cover layer 129 forms a fluid impermeable seal preventing fluids from contacting the internal components of acoustic sensor 125. To minimize front side external acoustic reflection during signal transmission and internal acoustic reflection during reception of acoustic echoes, cover layer 129 may comprise a material having an acoustic impedance matching the acoustic impedance of the external acoustic medium, such as fluids within production conduit 117.

Controller 120 may be a programmable electronic module that is communicatively coupled to the piezoelectric transducer(s) of the transmitter/receiver components within acoustic sensor 125. Controller 120 is configured, using electronics and program code instructions, to provide excitation pulse signals to the transducer electrodes during pulse transmit periods that may comprise the excitation phase of measurement cycles. Controller 120 includes a signal generator 127 and a signal processor 128. Signal generator 127 is configured using any combination of hardware and/or program code constructs to generate and send excitation pulse signals to electrodes 122 via communication interface 137 that may include one or more electrical conduction paths. Signal processor 128 is configured using any combination of hardware and/or program code constructs to detect/measure echo response signals received from receiver transducer electrodes via communication interface 137.

Signal generator 127 generates pulse signals comprising alternating current signals and corresponding voltage fluctuations that are applied to the transducer electrodes, resulting in fluctuating electrical fields and corresponding fluctuating electrical charges applied across the piezoelectric layer of the transducer within acoustic transmitter 116. Piezoelectric effect results in changes to mechanical stress and consequent mechanical deformation of the piezoelectric material layers. The mechanical deformation corresponds in terms of frequency and amplitude to the frequency and amplitude of the received electrical excitations signals, resulting in an ultrasonic vibration of the piezoelectric layer. The ultrasonic vibration of the piezoelectric layer mechanically induces corresponding ultrasonic pressure waves within and across wellbore 114. The acoustic pressure waves generated by the transmitter transducer, such as sensor pulse 138, propagate through a wellbore annulus 111 that includes all of the material layers and layer boundaries within wellbore 114. Sensor pulse 138 induces a corresponding acoustic echo signal 140 that results from reflection and/or refraction from various downhole acoustic boundaries within and at the boundaries between the various material layers within wellbore 114.

Sensor pulses, such as sensor pulse 138, are generated periodically, intermittently, or otherwise as part of individual measurement cycles. Each measurement cycle begins with an excitation phase during which signal generator 127 applies an electrical excitation that induces corresponding acoustic pulses in the transmitter transducer(s) to which the excitation is applied. Each measurement cycle further includes an echo response phase such as may be defined and implemented by signal processor components 128. During the echo response phase of each measurement cycle, signal processor components detect and process acoustic echo response signals such as signal 140 that are transduced by a receiver transducer from acoustic waves to an electrical acoustic response signal.

TTCE analysis requires acoustic response information that is location-specific (e.g., along the cylindrical boundary between cement layer 104 and casing 106) as well as properties specific (e.g., density, structural characteristics). The multiple different material layers that may present acoustic barriers (reflectors and sinks) and varying ambient environmental conditions may present interference for or otherwise reduce accuracy of the acoustic measurements and particularly acoustic measurements for which the target response locations are outside of one or more of the wellbore tubulars such as production tubing 110 and casing 106. TTCE apparatus 100 is configured to collect and process acoustic response information in a manner that removes interference such as extraneous acoustic response information and sensor variations to enable more accurate representation of target acoustic response information. The acoustic measurement components of TTCE apparatus 100 are configured to implement efficient and accurate acoustic measurements of wellbore material properties with reduced reliance on removing internal acoustic barriers such as production tubing.

In some embodiments, TTCE apparatus 100 is configured to collect acoustic measurement information that uses differential processing of acoustic responses to more precisely isolate intended acoustic response information such as cement bond response information. To this end, acoustic transmitter 116 comprises an azimuthally directional transmitter such as a unipole transmitter that emits substantially unidirectional acoustic pulses. Additionally or alternatively, acoustic receiver 118 comprises an azimuthally directional receiver such as a unipole receiver that receives acoustic signal energy unidirectionally. In such embodiments, acoustic transmitter 116 and acoustic receiver 118 may be azimuthally co-aligned to enable maximum directional (e.g., unidirectional) acoustic response information that eliminates or substantially reduces inter-azimuthal measurement variability.

The target points for acoustic measurements by the directional acoustic transmitter/receiver pair may be included along one or more circumferential boundaries at various radial distances from the center of wellbore 114. In the depicted embodiment, primary target points may be included in the cylindrical contact interface between cement layer 104 and the outer metallic surface of casing 106. Target points may also be included between the inner and outer surfaces of cement layer 104 and or within other material layers or material boundaries within wellbore 114. For example, target points may be included at the liquid/metal boundary between annular fluid layer 112 and casing 106 to test casing material properties such as calcium or other mineral buildup on the casing surface. All or most target points are located outside of production tubing 110 and some of the most important, such as cement-to-casing bond target points, are located outside of both production tubing 110 and casing 106.

Figure 2:
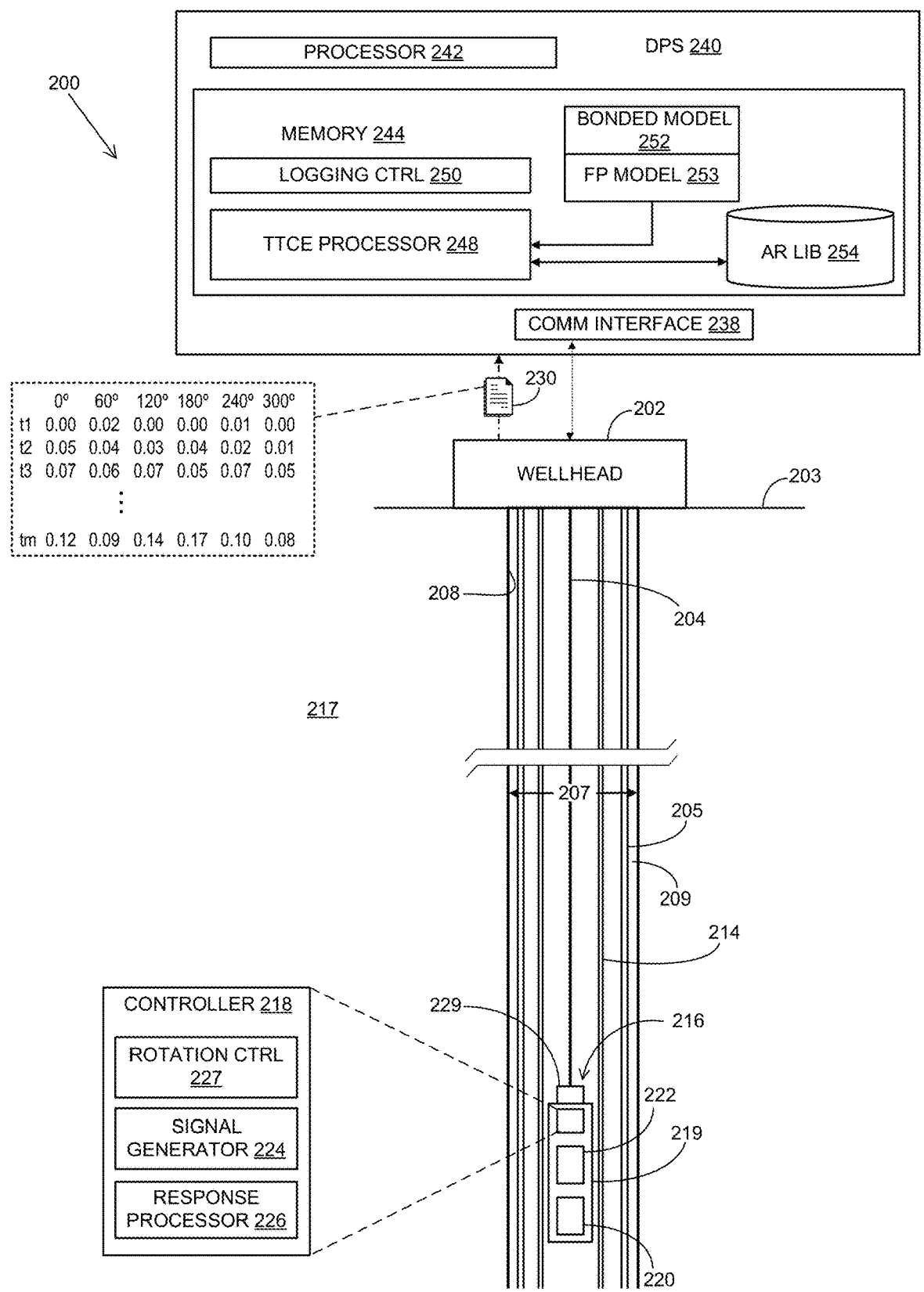
FIG. 2 is a high-level diagram depicting a well system that is configured to implement TTCE and other acoustic wellbore logging in accordance with some embodiments.

FIG. 2 is a high-level diagram depicting a well system 200 that is configured to implement TTCE and other acoustic wellbore logging in accordance with some embodiments. Well system 200 is particularly configured to address issues posed by TTCE, which entails measuring acoustic responses, such as acoustic echoes, generated by acoustic source signals that originate within an innermost tubing within a wellbore. Well system 200 includes subsystems, devices, and components configured to implement acoustic measurement testing procedures within a substantially cylindrical wellbore volume 207 that in the depicted embodiment is bounded and sealed by a casing 205. A cement layer 209 between casing 205 and an inner borehole wall 208 provides a protective seal that maintains structural and positional stability of casing 205. Well system 200 includes a wellhead 202 configured to deploy drilling and production and/or injection equipment such as drilling strings, production strings, etc. As shown, an interior tubing 214 is deployed within wellbore volume 207 and may comprise production tubing, drilling tubing such as drill pipes, injection tubing, or other type of tubing.

Wellhead 202 includes components for configuring and controlling deployment in terms of insertion and withdrawal of a test string within wellbore volume 207. The test string may be configured as a wireline test string deployed within interior tubing 214 and having a wireline cable 204 for moving and providing communication and power source connectivity for downhole test tools. In the depicted embodiment, wireline cable 204 is configured as the conveyance means for a logging tool 216 that includes an acoustic transmitter 220 and an acoustic receiver 222 disposed within a tool housing 219. Communication and power source couplings are provided to acoustic transmitter 220 and acoustic receiver 222 via wireline cable 204 having one or more communication and power terminals within wellhead 202.

Acoustic transmitter 220 and acoustic receiver 222 comprise components, including components not expressly depicted, configured to implement acoustic measurement testing including TTCE testing. Acoustic transmitter 220 may be configured as an acoustic transducer as depicted in FIG. 1B that transmits acoustic pulses in an azimuthally directional manner. Acoustic receiver 222 may comprise an azimuthally directional hydrophone configured to detect acoustic echoes resulting from the acoustic signals transmitted by acoustic transmitter 220. Logging tool 216 further includes a controller 218 comprising components including a signal generator 224 and a response processor 226 for controlling acoustic measurement operation. Signal generator 224 is configured to generate electrical signals that are converted by acoustic transmitter 220 into acoustic waves emitted within wellbore 207. Response processor 226 is configured to measure acoustic responses by processing the converted acoustic wave information from acoustic receiver 222.

Logging tool 216 is coupled via a telemetry link within wireline cable 204 to a data processing system (DPS) 240. DPS 240 includes a communication interface 238 configured to transmit and receive signals to and from logging tool 216 as well as other devices within well system 200 using a communication channel with wireline cable 204 as well as other telemetry links such as wireless electromagnetic links, acoustic links, etc. DPS 240 may be implemented in any of one or more of a variety of standalone or networked computer processing environments. As shown, DPS 240 may operate above a terrain surface 203 within or proximate to wellhead 202, for example. DPS 240 includes processing, memory, and storage components configured to receive and process acoustic measurement information to determine material and structural properties and conditions within and/or external to the cylindrical volume defined by borehole wall 208. DPS 240 is configured to receive acoustic response data from logging tool 216 as well as from other sources such as surface test facilities. The acoustic data received from logging tool 216 includes echo response signals detected by acoustic receiver 222. DPS 240 comprises, in part, a computer processor 242 and a memory device 244 configured to execute program instructions for controlling measurement cycles and processing the resultant echo response signals to determine wellbore material properties. Such properties and structural attributes may include but are not limited to cement structural integrity and the state of adhesion of the bonding between cement layer 209 and casing 205.

DPS 240 includes program components including a TTCE processor 248 and a logging controller 250. TTCE processor 248 includes program components and data configured to process acoustic response data received from logging tool 216. Logging controller 250 includes program components and data configured to coordinate and otherwise control positioning and repositioning of logging tool 216 within and along the length of interior tubing 214, as well as the acoustic measurement procedures at each position. Loaded and executing within memory 244, TTCE processor 248 is configured to receive and process acoustic response data such as logging data 230.

The components within DPS 240 and the test string interoperate to implement acoustic measurement collection and processing in a manner enabling optimal accuracy of through tubing material evaluation. A next acoustic measurement cycle may begin with positioning of logging tool 216 at a next axial location along the length of interior tubing 214. At the next axial location, logging tool 216 is rotationally positioned to an initial specified azimuthal angle. In the depicted embodiment, logging tool 216 may be rotated via controlled actuation of a DC motor 229. For example, a rotation controller 227 may be incorporated within controller 218 and be configured to azimuthally position logging tool 216, and more specifically the transmitter/receiver within logging tool 216, to a specified initial measurement azimuth angle.

The measurement cycle may continue with logging tool 216 measuring an acoustic response at the initial azimuthal angle. For TTCE logging, the overall acoustic response includes an echo response window in which echo signal characteristics profile material and structural characteristics of the cement-to-casing bonding at the azimuth angle. Following the initial azimuth measurement, logging tool 216 is rotated to a next azimuth at which a next azimuthally specific acoustic response is measured and otherwise collected, and the process is repeated at other azimuthal angles along a full 360° azimuthal path. The azimuthal angles at which the measurements are performed are selected to result in measurement pairs that are substantially azimuthally offset (e.g., one measurement is separated by at least 90° from the other measurement in the pair). In some embodiments, the measurement angles are selected to result in measurement pairs that are substantially azimuthally opposed (e.g., separated by approximately 180° within a range of 10°). It should be noted that the measurements at each point may be nearly instantaneous due to the proximity of the cement layer target points such that the rotation of acoustic tool 216 between measurements may be intermittent or continuous.

The azimuthal acoustic response is collected during a period over which the data at each of the azimuthal angles is recorded in association with the azimuthal angle and at a time point within an overall measurement time series. Response processor 226 may be configured to collect the time-specific and position-specific information into a time series matrix to be sent to and processed by DPS 240. In some embodiments, the matrix includes n columns and m rows wherein n is the number of azimuthal measurement positions separated by an azimuthal increment $\theta=360°/n$, and m is the number of time increments $\Delta t$ over a total measurement period T such that $m=T/\Delta t$. For example, acoustic response data 230 include a time series data matrix such as generated by logging tool 216. As shown, the matrix includes n=6 measurement positions including at azimuthal angles of 0°, 60°, 120°, 180°, 240°, and 300° at which a series of m time series measurements are performed.

The measured acoustic response data such as in the time series matrix format is received and processed by TTCE processor 248. TTCE processor 248 is configured using program instructions and data to process the acoustic response data to determine differential signal data that eliminates unnecessary and potentially interfering acoustic signal components that correspond with non-targeted material layers and structures within the wellbore. In some embodiments, TTCE processor 248 identifies, such as within a time series matrix, acoustic responses measured at offset azimuths. For instance, TTCE processor 248 may process acoustic response data 230 to identify the time series data measured at 0° and at 180° as one set pair of azimuthally offset acoustic measurements, the time series data measured at 60° and 240° as a second set pair of azimuthally offset acoustic measurements, and the time series data measured at 120° and 300° as a third set pair of azimuthally offset acoustic measurements.

To remove non-target response signal components, such as induced by the substantially azimuthally symmetrical interior tubing and casing layers, TTCE processor 248 generates a polar differential signal for each of the set pairs of measured signals. TTCE processor 248 may generate the polar differential signal as the amplitude difference between the raw measured values of the set pairs. For example, TTCE processor 248 may subtract the amplitude values 0.00, 0.05, 0.07 through 0.12 measured at 0° from the temporally corresponding amplitude values 0.00, 0.04, 0.05 through 0.10 to generate polar differential signals having amplitude values 0.00, −0.01, −0.02 through −0.02. In some embodiments, the time series raw measurement data may be transformed such as by signal filtration, Fourier transformation, Hilbert transformation, or other linear data transform technique. In such embodiments, TTCE processor 248 is configured to generate the polar differential signal as the difference between the respectively transformed time series measurement data for each of the offset measurement pairs.

TTCE processor 248 is further configured to process the polar differential signal data with model acoustic response data to determine a reference azimuth/azimuthal angle. In some embodiments, acoustic response models are loaded within memory 244 or otherwise accessible by TTCE processor 248. The models may be computer simulation models such as may include sets of equations having coefficients that are parameterized to simulate wellbore acoustic measurement testing. The coefficient parameters may include material properties and structures metrics and may include characteristics of a simulated acoustic transmitter and receiver. For TTCE applications, the models may be parameterized to simulate cement bonding characteristics and in some embodiments is configured to simulate acoustic responses corresponding to substantially ideal cement bonding characteristics.

In the depicted embodiment, a bonded AR model 252 and a free pipe AR model 253 are loaded within memory 244. Each of models 252 and 253 may be configured as a set of parameterized modeling equations that simulate downhole wellbore conditions such as material layers (e.g., material and dimensions of production tubing and casing) and also acoustic sensor characteristics. In addition to other properties and dimensions, models 252 and 253 are configured to simulate a respective cement layer characteristic. For instance, bonded AR model 252 is configured to simulate acoustic measurements in a wellbore environment in which the cement-to-casing bonding is maximum or otherwise optimal. In contrast, free pipe AR model 253 is configured to simulate acoustic measurements in a wellbore environment in which the cement-to-casing bonding is minimal or non-existent.

The acoustic response data from models 252 and 253 are output and stored in an AR model library 254 that is runtime accessible by TTCE processor 248 such as by static or dynamic program linking. In some embodiments, the modeled response data may be generated as measured acoustic response data from logging tool 216. For example, TTCE processor 248 may be configured to process acoustic response data from a point along the length of interior tubing 214 at which the cement-to-casing bonding has been determined to be maximum and also from a point at which the cement-to-casing bonding has been determined to be minimal or non-existent. Additionally or alternatively, the models such as models 252 and 253 may be configured with parameters determined based on acoustic or other measurements collected for a point along the length of interior tubing 214 at which the cement-to-casing bonding has been determined to be maximum and also from a point at which the cement-to-casing bonding has been determined to be minimal or non-existent.

To further isolate characteristics of a modeled target acoustic response, such as a cement bonding response, TTCE processor 248 is further configured to generate acoustic response differential data by comparing the acoustic response signals for one reference model with the acoustic response signals of another reference model. For example, TTCE processor 248 may generate the modeled differential signals by determining the amplitude difference between sets of acoustic response pairs from the response data from bonded AR model 252 and free pipe AR model 253. For example, the cumulative signal amplitude of acoustic response measurements for free pipe model 253 may be subtracted from a corresponding set of acoustic response amplitudes for bonded model 252 to generate a differential signal over a period that includes a cement bonding differential response.

TTCE processor 248 further includes program instructions for comparing the measured acoustic response data in the form of the polar differential signal data with the modeled acoustic response data to determine a reference azimuth for a given acoustic test position along the axial length of the wellbore. To determine a reference azimuth, TTCE processor 248 selects and retrieves one or more sets of modeled differential signals from AR model library 254. TTCE processor 248 may select the modeled differential signals based on the level of similarity between the wellbore conditions within wellbore volume 207 and acoustic sensor characteristics of logging tool 216 and the model from which the modeled differential signals were generated. TTCE processor 248 implements reference azimuth identification and selection by comparing the polar differential signals with corresponding modeled differential signals. For example, TTCE processor 248 may include program instructions for performing waveform matching to determine a closest match between each of the polar differential signals and a selected modeled differential signal. For TTCE analysis, TTCE processor 248 isolates a portion of each of the polar differential signal data and modeled differential signal data for comparison matching to determine one of the measurement azimuths having a cement bonding differential signature that most closely matches the modeled differential signal.

The acoustic responses at the identified reference azimuth are utilized as a location-specific reference by which acoustic responses at the other azimuths can be more accurately characterized. To this end, TTCE processor 248 is configured to determine differences between the measured acoustic responses at the reference azimuth and the measured acoustic responses at each of the other azimuths at the same axial location. For example, TTCE processor 248 may be configured to compute an amplitude difference between one or more acoustic signal components measured at the reference azimuth and one or more acoustic signal components measured at each of the other azimuths. For embodiments in which the time series polar differential data is generated from transformations of the raw measurement data, TTCE processor 248 is configured to generate corresponding transformed reference azimuth data that may be similarly differentiated (e.g., determine amplitude difference) with the transformed time series polar differential data.

The resultant difference data provides a mapping of a material compositional or structural condition/property for a target point (e.g., cement boundary) at the multiple measured azimuths for the axial location within interior tubing 214. This circumferential data may be further processed by TTCE processor 248 to determine a combined material compositional or structural condition/property at the axial location such as the level of cement bonding. For example, TTCE processor 248 may calculate a difference root mean square (RMS) comprising the RMS of the differences between the acoustic measurement at the reference azimuth and acoustic measurements at one or more other azimuths. TTCE processor 248 further calculates a measurement RMS comprising the RMS of the acoustic measurements at one or more other azimuths. TTCE processor 248 computes the material condition value by dividing the difference RMS by the measurement RMS to generate, for example, a cement bonding value associated with the axial location.

Figure 3:
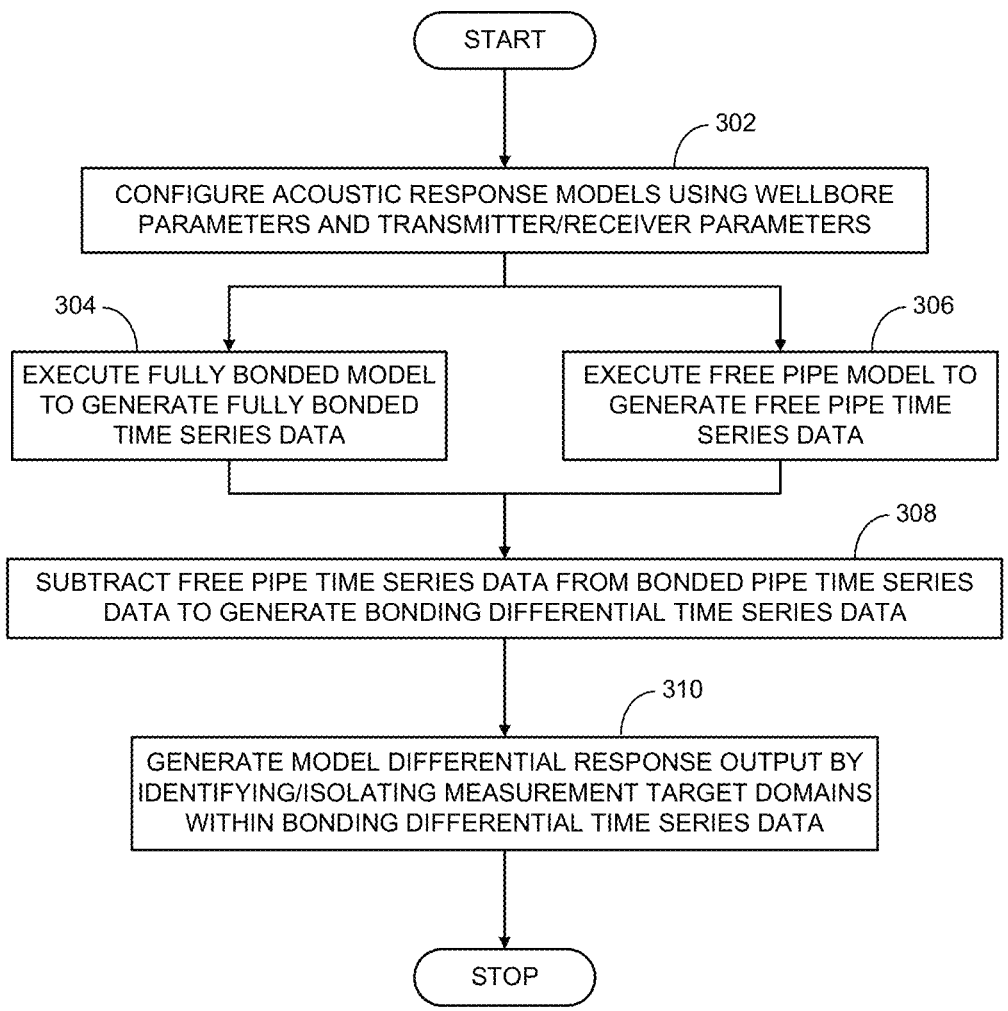
FIG. 3 is a flow diagram illustrating operations and functions for generating model differential acoustic responses in accordance with some embodiments.
Figure 5:
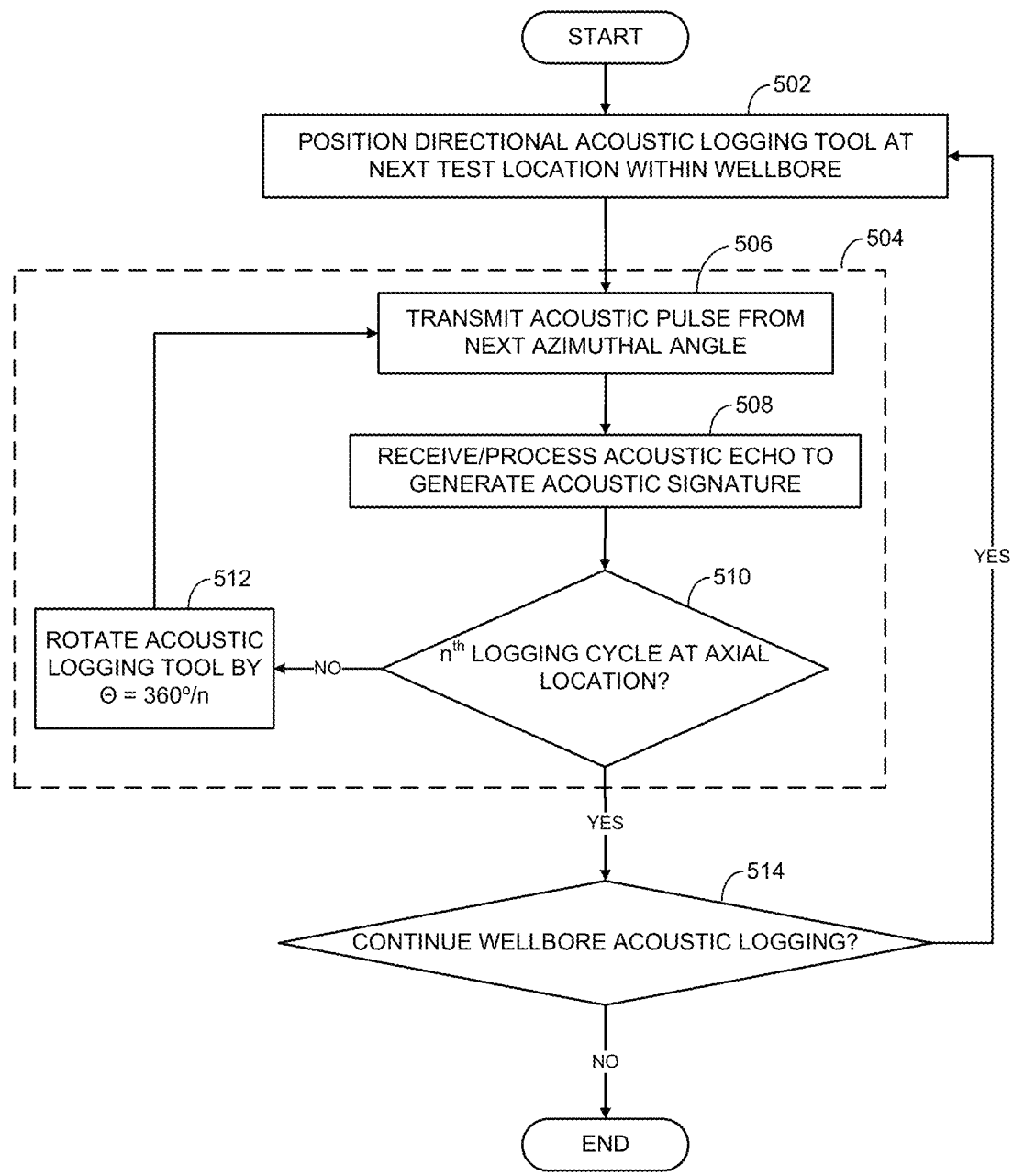
FIG. 5 is a flow diagram depicting operations and functions for generating azimuthal time series acoustic measurement data in accordance with some embodiments.
Figure 7:
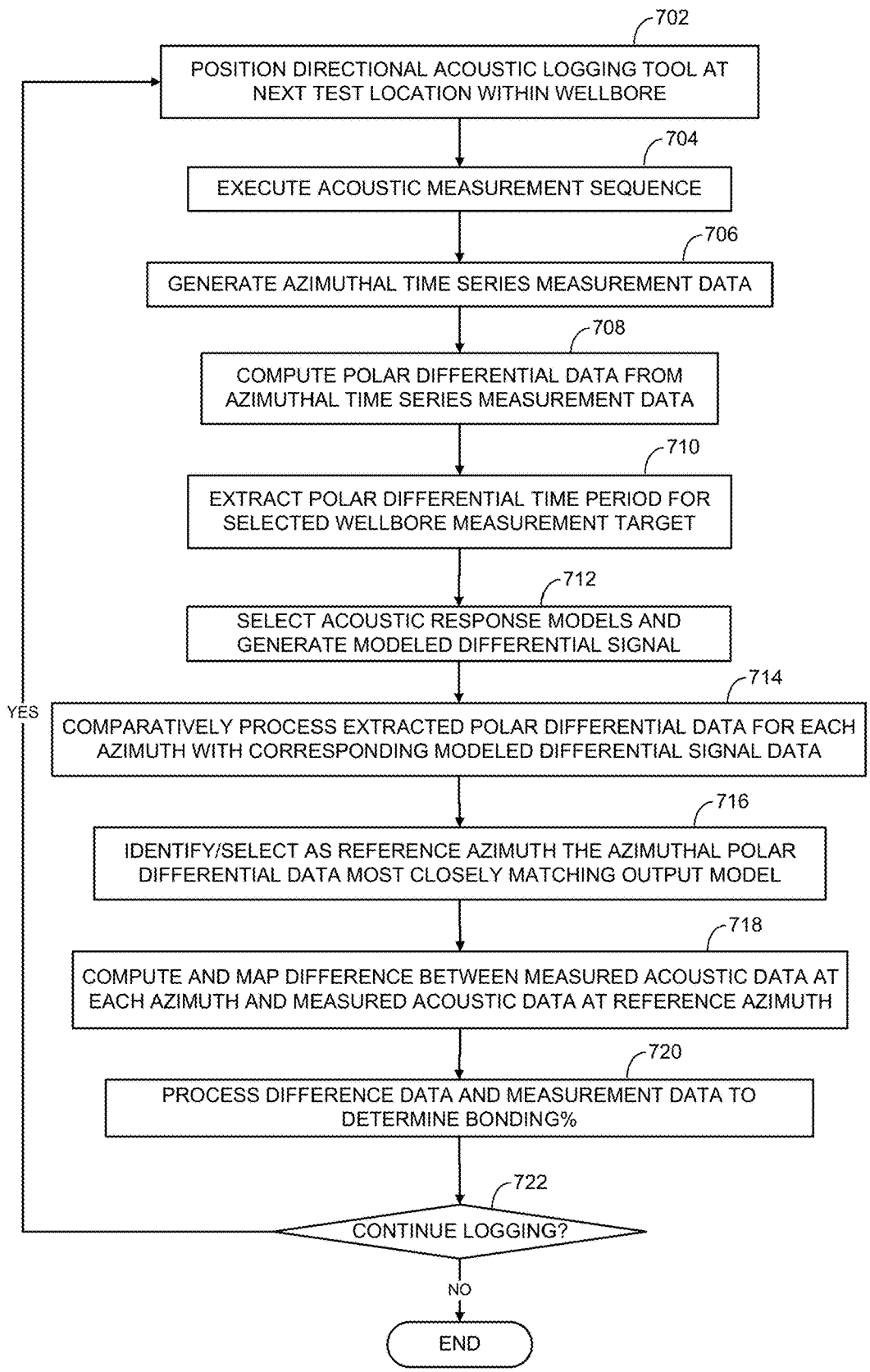
FIG. 7 is a flow diagram illustrating operations and functions for determining wellbore material properties using azimuthal polar differential processing in accordance with some embodiments.

FIGS. 3, 5, and 7 are flow diagrams illustrating operations and functions such as may be performed by an acoustic response processing apparatus and system such as depicted in FIGS. 1A, 1B, and 2. FIG. 3 is a flow diagram illustrating operations and functions for generating modeled differential acoustic responses in accordance with some embodiments. The process begins as shown at block 302 with a TTCE processor or other programmed component in the acoustic wellbore logging system configuring one or more acoustic response models. The models are configured using wellbore material properties and dimensions as well as transmitter/receiver parameters in some embodiments. For TTCE applications, the models include a bonded model that is parameterized and otherwise configured using metrics (e.g., coefficient values) that simulate wellbore material properties including a fully bonded cement to casing boundary and dimensions. The TTCE application models further include a free pipe model that is similarly configured using metrics that simulate wellbore material properties including a minimal or non-existent cement to casing bonding characteristic.

Figure 4A:
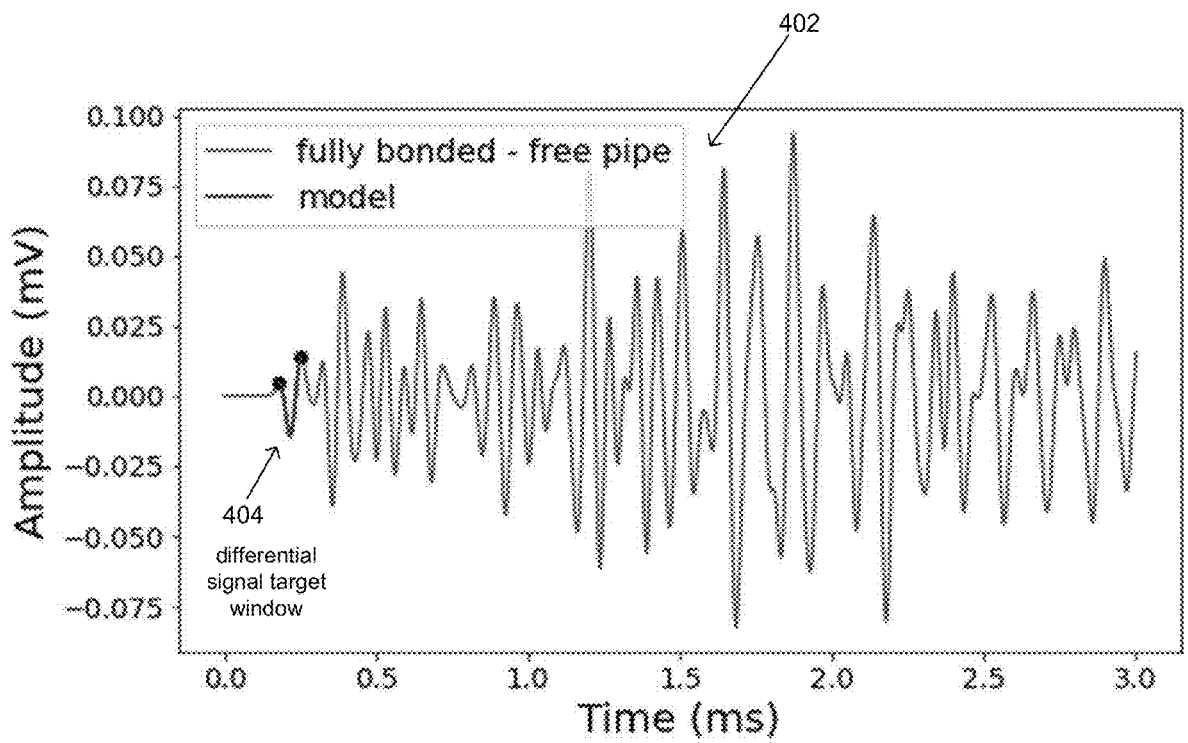
FIG. 4A depicts a model bonding differential signal in accordance with some embodiments.

At block 304, the TTCE processor calls or otherwise executes the bonded model to generate time series acoustic measurement data representing an acoustic response generated by a fully bonded cement-to-casing boundary. At block 306, the TTCE processor calls or otherwise executes the free pipe model to generate time series acoustic measurement data representing an acoustic response generated by a casing boundary surface having minimal or no cement-to-casing bonding. The process continues at block 308 with the TTCE processor determining a modeled differential signal between the modeled free pipe response and the modeled bonded response. For example, the TTCE processor may subtract or otherwise determine amplitude differences between the time series response data for the free pipe model and the time series response data for the bonded model. For embodiments in which time series polar differential data is generated from transformations of the raw measurement data, the TTCE processor is configured to generate corresponding transformed model response data that may be similarly differentiated (e.g., determine amplitude difference). FIG. 4A depicts a modeled differential signal 402 such as may be generated at block 308 in accordance with some embodiments.

Figure 4B:
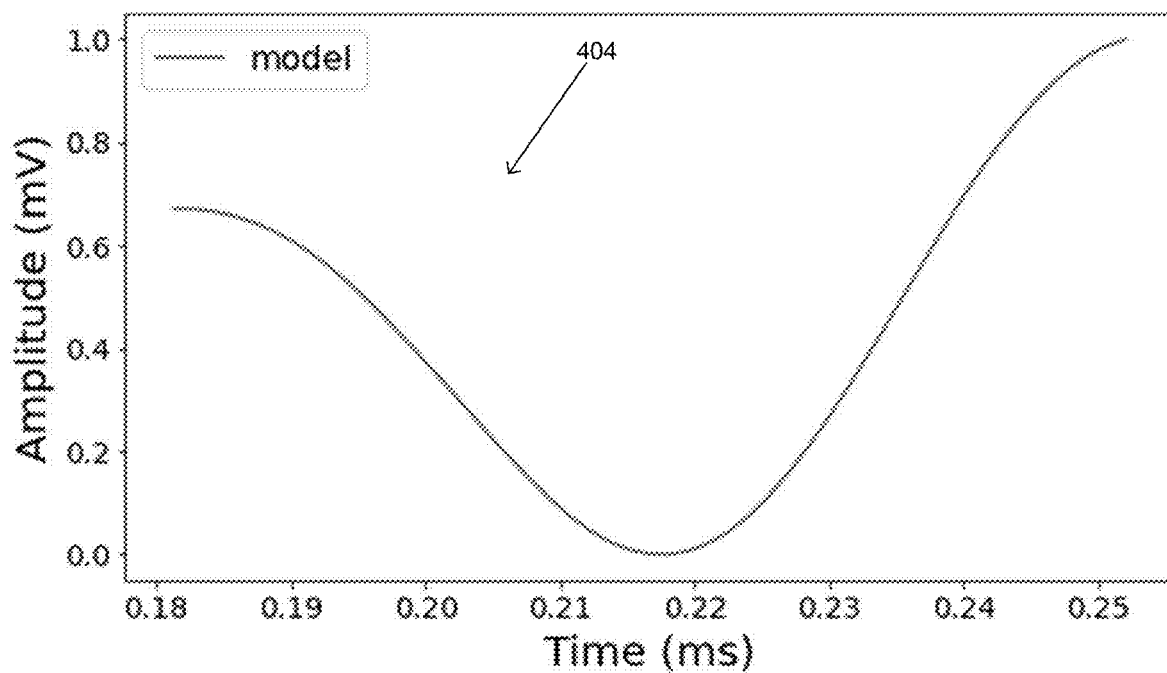
FIG. 4B illustrates a model differential signal for a specified acoustic target window in accordance with some embodiments.

At block 310, the TTCE processor generates a modeled differential echo response by identifying and isolating one or more target response domains from within the bonding differential time series data. For TTCE applications, TTCE processor generates a cement-to-casing bonding echo response by identifying and extracting the differential signal target window that corresponds to a cement bonding response window. For example, FIG. 4A depicts a cement-to-casing echo response window in which a model response signal 404 is identified and extracted as shown in FIG. 4B.

FIG. 5 is a flow diagram depicting operations and functions for generating azimuthal time series acoustic measurement data in accordance with some embodiments. The operations and functions depicted and described with reference to FIG. 5 may be performed by one or more of the systems and components depicted and described with reference to FIGS. 1A, 1B, and 2. The process begins as shown at block 502 with an acoustic logging tool/sensor positioned at a next axial location along the length of a wellbore. For TTCE applications, well system components such as wireline or slickline control components may be utilized to reposition the logging tool axially within an interior tubing such as a production tubing that is disposed within multiple annular material layers such as fluid, tubing, and cement layers.

At block 504, the well system executes an acoustic measurement sequence at the next axial position. The sequence begins at block 506 with the logging tool transmitting an acoustic pulse with the acoustic transmitter aligned at a specified azimuthal position (e.g., from a first specified azimuthal angle). In some embodiments, the acoustic transmitter comprises a directional transmitter such as a unipolar transmitter that transmits unidirectionally. At block 508, an acoustic receiver within the logging tool that is also aligned at the specified azimuthal angle receives an acoustic echo response that may be further processed such as by a TTCE processor to isolate a cement-to-casing acoustic response from within the overall response. In some embodiments, the acoustic receiver is a directional receiver such as a unipolar receiver that receives unidirectionally.

The acoustic measurement sequence continues as shown at block 510 with a determination of whether the full azimuthal measurement cycle (i.e., measurements at n azimuthal angles) has been completed for the axial location. If not, control passes to block 512 with a well system control component rotating the acoustic logging tool by a specified azimuthal increment angle $\theta=360°/n$, wherein n represents the number of azimuthal locations at which the acoustic logging tool measures acoustic responses at each axial location. More specifically, the acoustic tool rotation includes rotating the directional transmission face of the acoustic transmitter and the directional receiving face of the acoustic receiver to the next azimuthal angle position. Typical azimuth rotation increments may be 5° or 10° for example. The measurements at each azimuthal angle may be nearly instantaneous due to the proximity of the specified target points to the acoustic transmitter and receiver such that the rotation of the acoustic tool between measurements may be intermittent or continuous.

Figure 6:
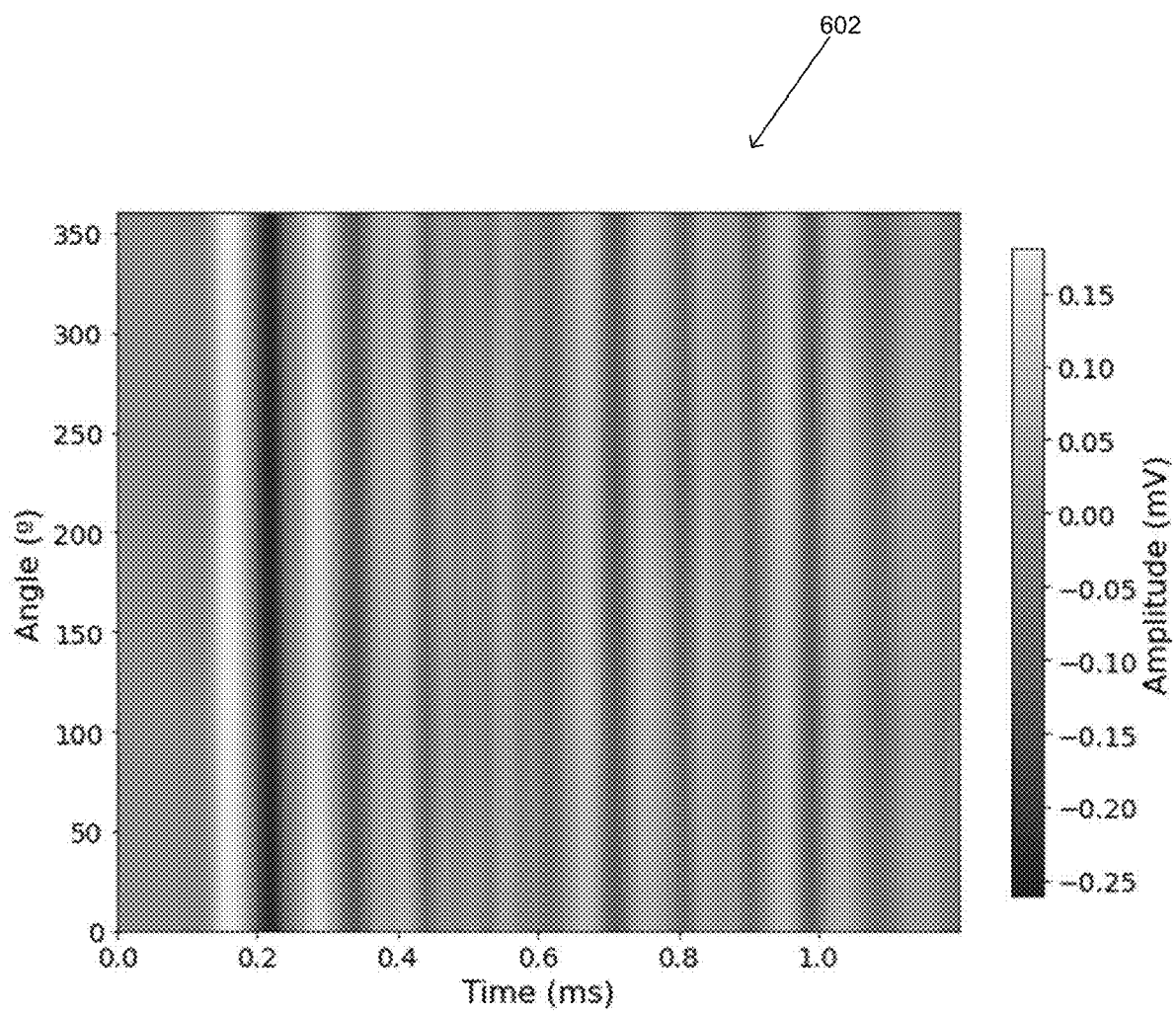
FIG. 6 illustrates mapped acoustic measurement data in accordance with some embodiments.

A next measurement cycle begins following the azimuthal repositioning. In response to all n measurements completed as determined at block 510, control passes to block 514 with the acoustic logging system determining whether to continue acoustic logging. If so, control passes back to block 502 and if not the process ends. The acoustic response measurement results may be mapped as time series data such as depicted in FIG. 6. Specifically, FIG. 6 illustrates acoustic measurement data 602 that is mapped as signal strength (amplitude) as the level of shading over as a time series and azimuthal angle matrix.

The acoustic measurement data mapped as a time series by azimuthal measurement angle is further processed to provide a location-based reference enabling efficient and accurate correlation of measurement results to wellbore material properties at specified target locations such as the cement-to-casing boundary. FIG. 7 is a flow diagram illustrating operations and functions for determining downhole material properties/conditions using azimuthal polar differential processing. The operations and functions depicted and described with reference to FIG. 7 may be performed by one or more systems and components depicted and described with reference to FIGS. 1A, 1B, 2, 3, and 5. The process begins at block 702 with the logging system positioning an acoustic logging tool at a next axial test location along the length of a wellbore. The acoustic logging tool comprises a directional transmitter and a directional receiver for implementing directional acoustic measurements at selected azimuthal angles.

Figure 8:
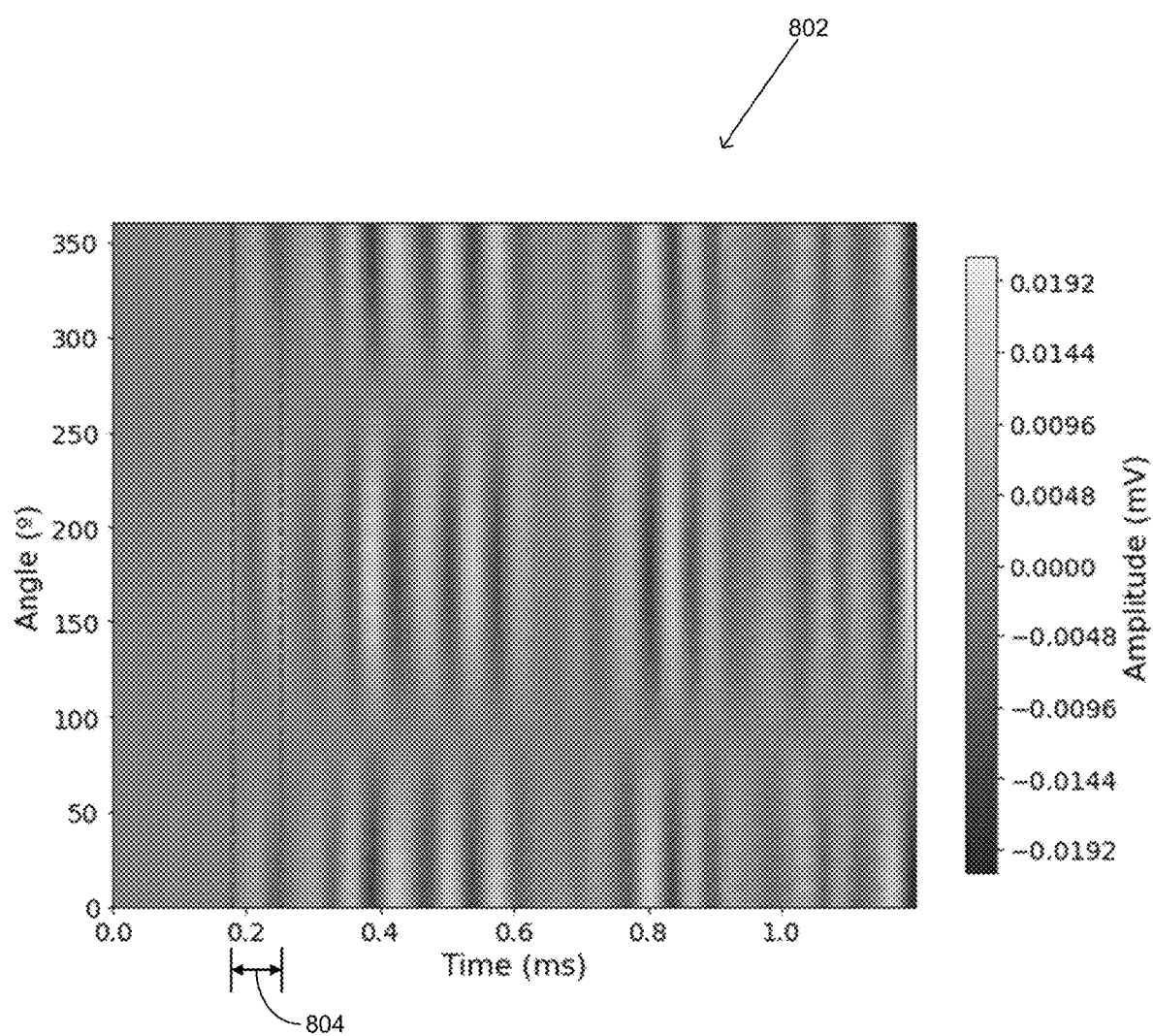
FIG. 8 depicts mapped polar differential data in accordance with some embodiments.
Figure 9:
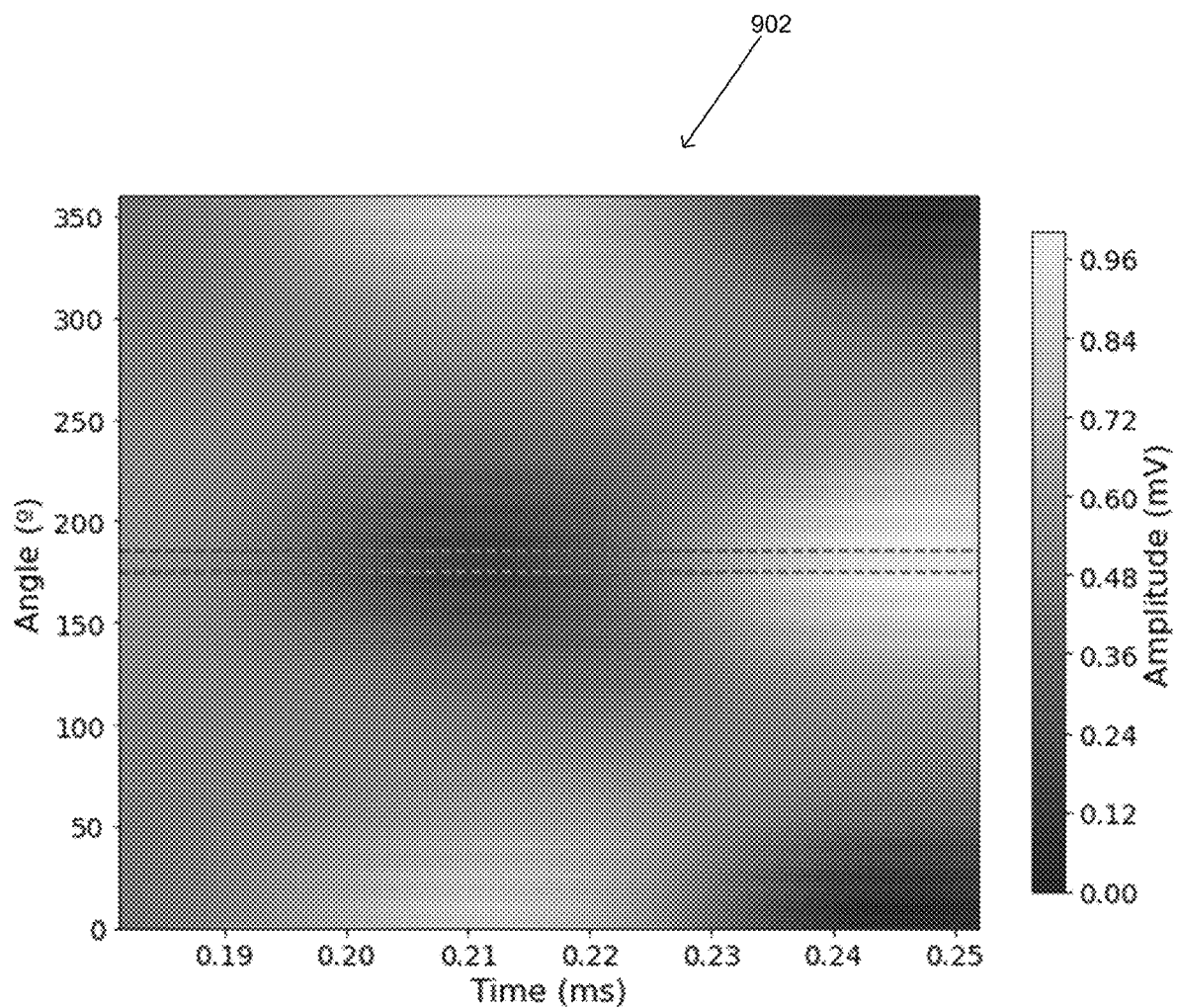
FIG. 9 illustrates polar differential data within and extracted from an acoustic target window in accordance with some embodiments.

At block 704, the acoustic logging system executes an acoustic measurement sequence such as depicted and described with reference to block 504 in FIG. 5. The system processes the resultant time series data to generate azimuthal time series measurement data corresponding to measurement time increments and to azimuthal measurement position (block 706). At block 708, the logging system processes the azimuthal time series data to generate polar differential data. As described with reference to FIG. 2, the polar differential data may comprise a polar differential signal generated by determining the difference, such as via subtraction, between azimuthally offset (e.g., substantially diametrically opposed) acoustic measurements. As shown in FIG. 8, resultant polar differential signal data 802 for the entire measurement period may be mapped to azimuthal measurement position. As shown, polar differential signal 802 includes a target echo response window 804 that may correspond to a cement bond echo response window. At block 710, the polar differential signal data within a target response window such as window 804, is identified and extracted. For example, FIG. 9 illustrates polar differential data 902 within and extracted from window 804.

The process continues at block 712 with a logging system component such as a TTCE processor selecting one or more acoustic response (AR) models to be used for comparative processing in combination with the polar differential signal data. For a TTCE application, the TTCE processor selects a bonded AR model and a free pipe AR model with each configured as a set of parameterized modeling equations that simulate downhole wellbore conditions such as material layers and also acoustic sensor characteristics. The bonded AR model is configured to simulate acoustic measurements in a wellbore environment in which the cement-to-casing bonding is maximum or otherwise optimal. The free pipe AR model is configured to simulate acoustic measurements in a wellbore environment in which the cement-to-casing bonding is minimal or non-existent. Also at block 712, the TTCE processor generates modeled differential signal output as depicted and described with reference to blocks 308 and 310 in FIG. 3.

Figure 10:
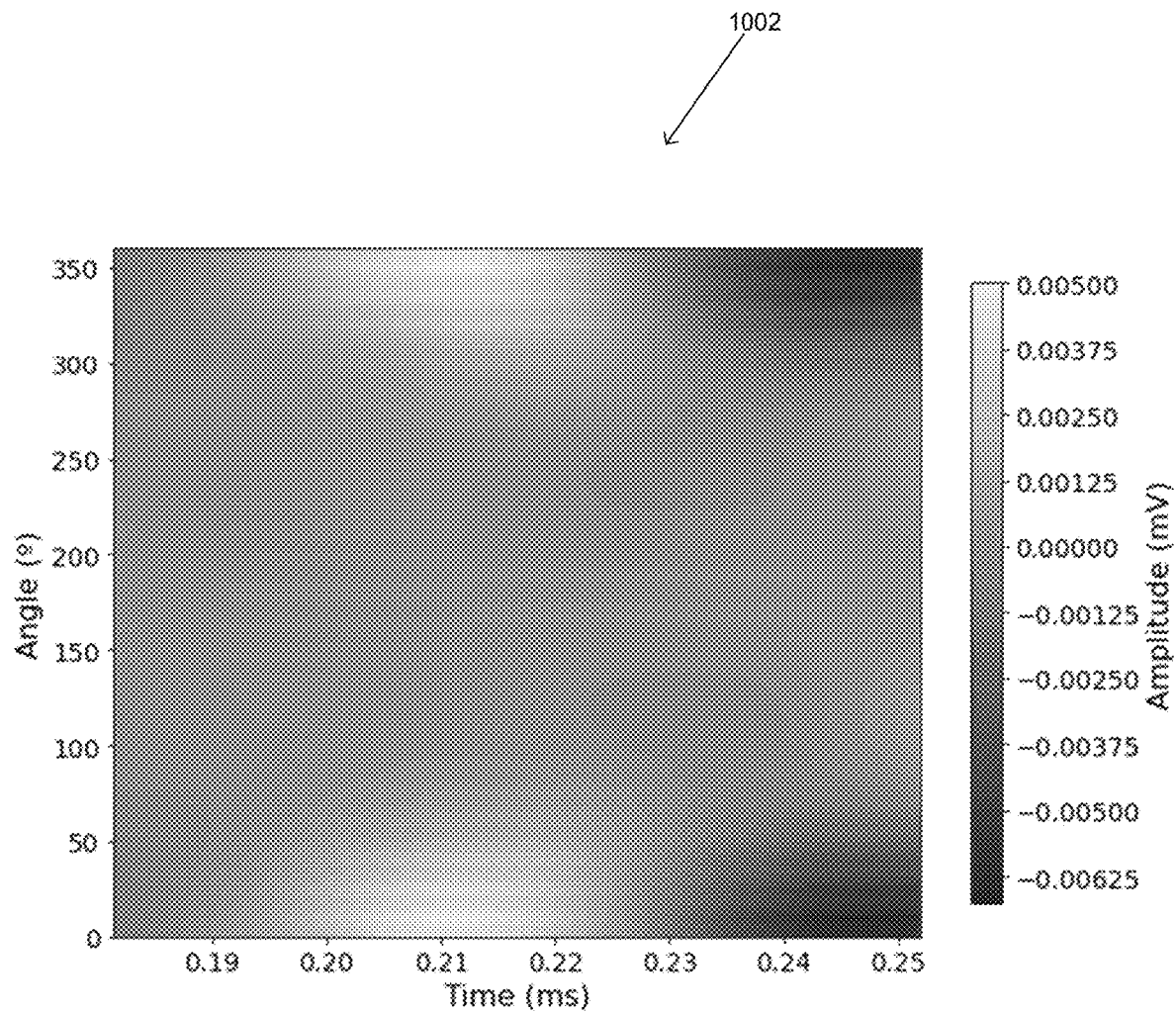
FIG. 10 depicts mapped reference differential data in accordance with some embodiments.

At block 714, the TTCE processor comparatively processes the extracted polar differential data across the measurement azimuths with corresponding modeled differential signal data to identify a reference azimuth. In some embodiments, the TTCE processor compares at least a portion of the modeled bonding differential signal (e.g., a cement bond echo response window) to a temporally corresponding portion of each of the measured polar differential signals. In some embodiments, the TTCE processor calls or otherwise executes a waveform matching programmed algorithm to determine similarity values for each comparison. At block 716, the TTCE processor identifies and selects one of the measurement azimuths to be a reference azimuth based on the similarity values. For example, the TTCE processor may compare the similarity values computed for each of the measurement azimuths to determine the reference azimuth. At block 718, the TTCE processor computes and maps differences between the measured acoustic response generated at block 706 for each of the azimuths and the measured acoustic response at the reference azimuth. For example, FIG. 10 depicts mapped reference differential data 1002 that represents the amplitude differences between the time series of acoustic responses at the reference azimuth and the time series of acoustic responses at each of the other measurement azimuths.

Figure 11:
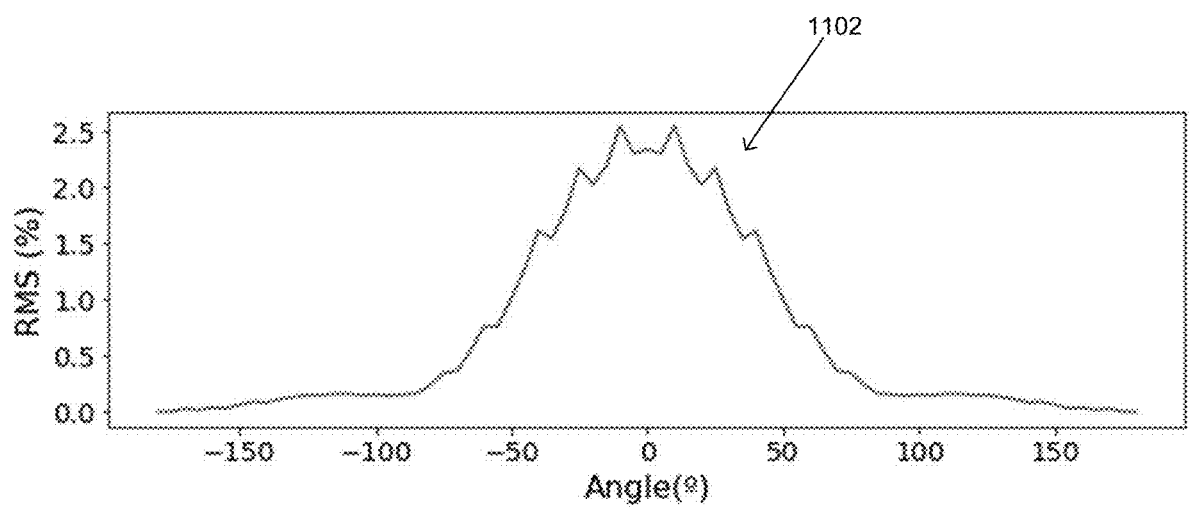
FIG. 11 illustrates RMS data generated from mapped reference differential data in accordance with some embodiments.

At block 720, the TTCE processor computes wellbore material properties such as cement bonding level/quality using the difference data generated at block 718. For example, the TTCE processor may be configured to comparatively process the azimuthal acoustic measurements and the differences between the acoustic measurements at the reference azimuth and the acoustic measurements at the other azimuths using sum of absolute values or other normalization distribution techniques to generate values characterizing material properties. In some embodiments, the TTCE processor may utilize RMS normalization to perform the comparative processing. For example, the TTCE processor may compute an RMS (%) in accordance with the relation: RMS (%)=100(Difference_RMS/Raw_RMS). Difference_RMS represents a difference RMS value comprising the RMS of the differences between the acoustic measurements at the reference azimuth and acoustic measurements at the other azimuths. Raw_RMS represents a measurement RMS value comprising the RMS of the raw acoustic measurement at each azimuth. For example, FIG. 11 illustrates RMS data 1102 generated from mapped reference differential data and the raw measurement data in accordance with some embodiments. Control may pass from inquiry block 722 back to block 702 for additional logging operations at a next axial wellbore position. It should be noted that the acoustic response and modeling processing operations depicted in blocks 708 through 720 may be implemented as post-logging operations following multiple acoustic measurement cycles at different axial positions within the wellbore.

Example Computer

Figure 12:
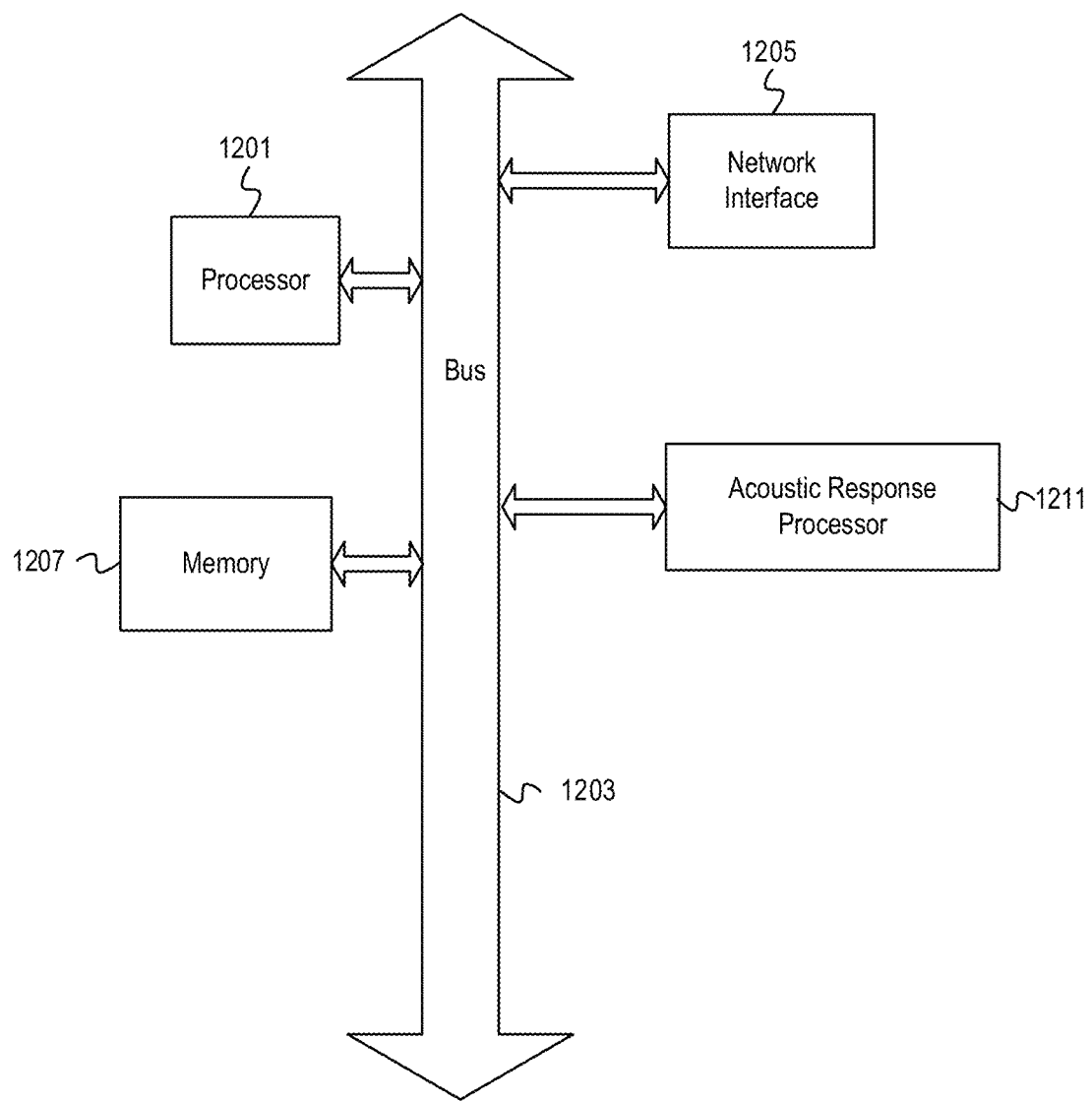
FIG. 12 depicts an example computer configured to implement acoustic wellbore logging in accordance with some embodiments.

FIG. 12 depicts an example computer system, according to some embodiments. The computer includes a processor 1201. The computer includes memory 1207, a bus 1203, and a network interface 1205 (e.g., a wireless interface, interface for a wired connection, etc.). The computer also includes an acoustic response processor 1211. Acoustic response processor 1211 may be configured to perform the different signal processing as described above. Any one of the previously described functionalities may be partially (or entirely) implemented in hardware and/or on the processor 1201. For example, the functionality may be implemented with an application specific integrated circuit, in logic implemented in the processor 1201, in a co-processor on a peripheral device or card, etc. Further, realizations may include fewer or additional components not illustrated in FIG. 12. The processor 1201 and the network interface 1205 are coupled to the bus 1203. Although illustrated as being coupled to the bus 1203, the memory 1207 may be coupled to the processor 1201.

The flowcharts are provided to aid in understanding the illustrations and are not to be used to limit scope of the claims. The flowcharts depict example operations that can vary within the scope of the claims. Additional operations may be performed; fewer operations may be performed; the operations may be performed in parallel; and the operations may be performed in a different order. It will be understood that each block of the flowchart illustrations and/or block diagrams, and combinations of blocks in the flowchart illustrations and/or block diagrams, can be implemented by program code. The program code may be provided to a processor of a general-purpose computer, special purpose computer, or other programmable machine or apparatus. It will be understood that each block of the flowchart illustrations and/or block diagrams, and combinations of blocks in the flowchart illustrations and/or block diagrams, can be implemented by program code. The program code may be provided to a processor of a general-purpose computer, special purpose computer, or other programmable machine or apparatus.

The machine-readable medium may be a machine-readable signal medium or a machine-readable storage medium. A machine-readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine-readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium may be any tangible medium that can store a program for use by or in connection with an instruction execution system, apparatus, or device.

Program code/instructions may also be stored in a machine-readable medium that can direct a machine to function in a particular manner, such that the instructions stored in the machine-readable medium produce an article of manufacture including instructions which implement the function/act specified in the flowchart and/or block diagram block or blocks. Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components. These and other variations, modifications, additions, and improvements may fall within the scope of the disclosure. As used herein, the term "or" is inclusive unless otherwise explicitly noted. Thus, the phrase "at least one of A, B, or C" is satisfied by any element from the set {A, B, C} or any combination thereof, including multiples of any element.

EXAMPLE EMBODIMENTS

Embodiment 1: A method comprising: determining a polar differential signal for each of one or more pairs of azimuthally offset acoustic measurements within a wellbore; identifying a reference azimuth based, at least in part, on comparing the polar differential signals to a modeled bonding differential signal within a target response window; determining differences between an acoustic measurement at the reference azimuth and acoustic measurements at one or more other azimuths; and determining a wellbore material condition based, at least in part, on the determined differences. Said determining a polar differential signal may comprise computing an amplitude difference between one or more acoustic signal components measured at a first azimuth and one or more acoustic signal components measured at a second azimuth that is azimuthally offset from the first azimuth. The method may further comprise generating the one or more pairs of azimuthally offset acoustic measurements including: positioning an azimuthally directional acoustic sensor at a first axial location along the wellbore; at the first axial location, measuring acoustic responses at a first set of one or more azimuthal angles; and at the first axial location, measuring acoustic responses at a second set of one or more azimuthal angles, wherein each of the second set of one or more azimuthal angles is at least 90° offset from a respective one of the first set of one or more azimuthal angles. The azimuthal wellbore material condition may be a cement bonding condition, and the method may further comprise generating a bonded response from a bonded acoustic response model and a free pipe response from a free pipe acoustic response model, wherein the bonded acoustic response model and the free pipe acoustic response model are configured using wellbore parameters; and generating the modeled differential signal by subtracting the free pipe response from the bonded response. Said identifying a reference azimuth may include comparing at least a portion of the modeled bonding differential signal to a temporally corresponding portion of each of the polar differential signals; and selecting as the reference azimuth, the azimuth at which a closest match is determined between the portion of the modeled bonding differential signal and the temporally corresponding portion of a polar differential signal. The portion of the modeled bonding differential signal and the temporally corresponding portion of each of the polar differential signals may comprise a cement boundary echo window. Determining differences between an acoustic measurement at the reference azimuth and acoustic measurements at one or more other azimuths may include for each of the one or more other azimuths, computing an amplitude difference between one or more acoustic signal components measured at the reference azimuth and one or more acoustic signal components measured at the other azimuth. The method may further comprise collecting the one or more pairs of azimuthally offset acoustic measurements at an axial location along the wellbore, wherein the wellbore material condition comprises a cement bonding condition, and wherein said determining the wellbore material condition based, at least in part, on the determined differences includes: calculating a difference root mean square (RMS) comprising the RMS of the differences between the acoustic measurement at the reference azimuth and acoustic measurements at one or more other azimuths; calculating a measurement RMS comprising the RMS of the acoustic measurements at one or more other azimuths; and dividing the difference RMS by the measurement RMS to generate a cement bonding value associated with the axial location.

Embodiment 2: A system comprising: a processor; and a computer-readable medium having instructions stored thereon that are executable by the processor to cause the system to, determine a polar differential signal for each of one or more pairs of azimuthally offset acoustic measurements within a wellbore; identify a reference azimuth based, at least in part, on comparing the polar differential signals to a modeled bonding differential signal within a target response window; determine differences between an acoustic measurement at the reference azimuth and acoustic measurements at one or more other azimuths; and determine a wellbore material condition based, at least in part, on the determined differences. The instructions executable by the processor to cause the system to determine a polar differential signal may comprise instructions executable by the processor to cause the system to compute an amplitude difference between one or more acoustic signal components measured at a first azimuth and one or more acoustic signal components measured at a second azimuth that is azimuthally offset from the first azimuth. The instructions may further comprise instructions executable by the processor to cause the system to generate the one or more pairs of azimuthally offset acoustic measurements including: positioning an azimuthally directional acoustic sensor at a first axial location along the wellbore; at the first axial location, measuring acoustic responses at a first set of one or more azimuthal angles; and at the first axial location, measuring acoustic responses at a second set of one or more azimuthal angles, wherein each of the second set of one or more azimuthal angles is at least 90° offset from a respective one of the first set of one or more azimuthal angles. The azimuthal wellbore material condition may be a cement bonding condition, and the instructions may include instructions executable by the processor to cause the system to: generate a bonded response from a bonded acoustic response model and a free pipe response from a free pipe acoustic response model, wherein the bonded acoustic response model and the free pipe acoustic response model are configured using wellbore parameters; and generate the modeled differential signal by subtracting the free pipe response from the bonded response. Identifying a reference azimuth may include: comparing at least a portion of the modeled bonding differential signal to a temporally corresponding portion of each of the polar differential signals; and selecting as the reference azimuth, the azimuth at which a closest match is determined between the portion of the modeled bonding differential signal and the temporally corresponding portion of a polar differential signal. The portion of the modeled bonding differential signal and the temporally corresponding portion of each of the polar differential signals may comprise a cement boundary echo window. The instructions may include instructions executable by the processor to cause the system to collect the one or more pairs of azimuthally offset acoustic measurements at an axial location along the wellbore, wherein the wellbore material condition comprises a cement bonding condition, and wherein determining the wellbore material condition based, at least in part, on the determined differences includes: calculating a difference root mean square (RMS) comprising the RMS of the differences between the acoustic measurement at the reference azimuth and acoustic measurements at one or more other azimuths; calculating a measurement RMS comprising the RMS of the acoustic measurements at one or more other azimuths; and dividing the difference RMS by the measurement RMS to generate a cement bonding value associated with the axial location.

Embodiment 3: A non-transitory, computer-readable medium having instructions stored thereon that are executable by a computing device to perform operations comprising: determining a polar differential signal for each of one or more pairs of azimuthally offset acoustic measurements within a wellbore; identifying a reference azimuth based, at least in part, on comparing the polar differential signals to a modeled bonding differential signal within a target response window; determining differences between an acoustic measurement at the reference azimuth and acoustic measurements at one or more other azimuths; and determining a wellbore material condition based, at least in part, on the determined differences. The azimuthal wellbore material condition may be a cement bonding condition, and the instructions may include instructions executable by the processor to cause the system to: generate a bonded response from a bonded acoustic response model and a free pipe response from a free pipe acoustic response model, wherein the bonded acoustic response model and the free pipe acoustic response model are configured using wellbore parameters; and generate the modeled differential signal by subtracting the free pipe response from the bonded response. Identifying a reference azimuth may include: comparing at least a portion of the modeled bonding differential signal to a temporally corresponding portion of each of the polar differential signals; and selecting as the reference azimuth, the azimuth at which a closest match is determined between the portion of the modeled bonding differential signal and the temporally corresponding portion of a polar differential signal. The portion of the modeled bonding differential signal and the temporally corresponding portion of each of the polar differential signals may comprise a cement boundary echo window. The instructions may include instructions executable by the processor to cause the system to collect the one or more pairs of azimuthally offset acoustic measurements at an axial location along the wellbore, wherein the wellbore material condition comprises a cement bonding condition, and wherein determining the wellbore material condition based, at least in part, on the determined differences includes: calculating a difference root mean square (RMS) comprising the RMS of the differences between the acoustic measurement at the reference azimuth and acoustic measurements at one or more other azimuths; calculating a measurement RMS comprising the RMS of the acoustic measurements at one or more other azimuths; and dividing the difference RMS by the measurement RMS to generate a cement bonding value associated with the axial location.

The invention claimed is:

1. A method comprising:
   determining a polar differential signal for each of one or more pairs of azimuthally offset acoustic measurements within a wellbore;
   identifying a reference azimuth based, at least in part, on comparing the polar differential signals to a modeled bonding differential signal within a target response window;
   determining differences between an acoustic measurement at the reference azimuth and acoustic measurements at one or more other azimuths; and
   determining a wellbore material condition based, at least in part, on the determined differences.

2. The method of claim 1, wherein said determining a polar differential signal comprises computing an amplitude difference between one or more acoustic signal components measured at a first azimuth and one or more acoustic signal components measured at a second azimuth that is azimuthally offset from the first azimuth.

3. The method of claim 1, further comprising generating the one or more pairs of azimuthally offset acoustic measurements including:
   positioning an azimuthally directional acoustic sensor at a first axial location along the wellbore;
   at the first axial location, measuring acoustic responses at a first set of one or more azimuthal angles; and
   at the first axial location, measuring acoustic responses at a second set of one or more azimuthal angles, wherein each of the second set of one or more azimuthal angles is at least 90° offset from a respective one of the first set of one or more azimuthal angles.

4. The method of claim 1, wherein the wellbore material condition is a cement bonding condition, said method further comprising:
   generating a bonded response from a bonded acoustic response model and a free pipe response from a free pipe acoustic response model, wherein the bonded acoustic response model and the free pipe acoustic response model are configured using wellbore parameters; and generating the modeled differential signal by subtracting the free pipe response from the bonded response.

5. The method of claim 4, wherein said identifying a reference azimuth includes:
   comparing at least a portion of the modeled bonding differential signal to a temporally corresponding portion of each of the polar differential signals; and
   selecting as the reference azimuth, the azimuth at which a closest match is determined between the portion of the modeled bonding differential signal and the temporally corresponding portion of a polar differential signal.

6. The method of claim 5, wherein the portion of the modeled bonding differential signal and the temporally corresponding portion of each of the polar differential signals comprises a cement boundary echo window.

7. The method of claim 1, wherein determining differences between an acoustic measurement at the reference azimuth and acoustic measurements at one or more other azimuths includes for each of the one or more other azimuths, computing an amplitude difference between one or more acoustic signal components measured at the reference azimuth and one or more acoustic signal components measured at the other azimuth.

8. The method of claim 1, further comprising collecting the one or more pairs of azimuthally offset acoustic measurements at an axial location along the wellbore, wherein the wellbore material condition comprises a cement bonding condition, and wherein said determining the wellbore material condition based, at least in part, on the determined differences includes:
   calculating a difference root mean square (RMS) comprising the RMS of the differences between the acoustic measurement at the reference azimuth and acoustic measurements at one or more other azimuths;
   calculating a measurement RMS comprising the RMS of the acoustic measurements at one or more other azimuths; and
   dividing the difference RMS by the measurement RMS to generate a cement bonding value associated with the axial location.

9. A system comprising:
   a processor; and
   a computer-readable medium having instructions stored thereon that are executable by the processor to cause the system to,
      determine a polar differential signal for each of one or more pairs of azimuthally offset acoustic measurements within a wellbore;
      identify a reference azimuth based, at least in part, on comparing the polar differential signals to a modeled bonding differential signal within a target response window;
      determine differences between an acoustic measurement at the reference azimuth and acoustic measurements at one or more other azimuths; and
      determine a wellbore material condition based, at least in part, on the determined differences.

10. The system of claim 9, wherein the instructions executable by the processor to cause the system to determine a polar differential signal comprise instructions executable by the processor to cause the system to compute an amplitude difference between one or more acoustic signal components measured at a first azimuth and one or more acoustic signal components measured at a second azimuth that is azimuthally offset from the first azimuth.

11. The system of claim 9, wherein the instructions further comprise instructions executable by the processor to cause the system to generate the one or more pairs of azimuthally offset acoustic measurements including:
   positioning an azimuthally directional acoustic sensor at a first axial location along the wellbore;
   at the first axial location, measuring acoustic responses at a first set of one or more azimuthal angles; and
   at the first axial location, measuring acoustic responses at a second set of one or more azimuthal angles, wherein each of the second set of one or more azimuthal angles is at least 90° offset from a respective one of the first set of one or more azimuthal angles.

12. The system of claim 9, wherein the wellbore material condition is a cement bonding condition, and wherein the instructions include instructions executable by the processor to cause the system to:
   generate a bonded response from a bonded acoustic response model and a free pipe response from a free pipe acoustic response model, wherein the bonded acoustic response model and the free pipe acoustic response model are configured using wellbore parameters; and
   generate the modeled differential signal by subtracting the free pipe response from the bonded response.

13. The system of claim 12, wherein identifying a reference azimuth includes:
   comparing at least a portion of the modeled bonding differential signal to a temporally corresponding portion of each of the polar differential signals; and
   selecting as the reference azimuth, the azimuth at which a closest match is determined between the portion of the modeled bonding differential signal and the temporally corresponding portion of a polar differential signal.

14. The system of claim 13, wherein the portion of the modeled bonding differential signal and the temporally corresponding portion of each of the polar differential signals comprises a cement boundary echo window.

15. The system of claim 9, wherein the instructions include instructions executable by the processor to cause the system to collect the one or more pairs of azimuthally offset acoustic measurements at an axial location along the wellbore, wherein the wellbore material condition comprises a cement bonding condition, and wherein determining the wellbore material condition based, at least in part, on the determined differences includes:
   calculating a difference root mean square (RMS) comprising the RMS of the differences between the acoustic measurement at the reference azimuth and acoustic measurements at one or more other azimuths;
   calculating a measurement RMS comprising the RMS of the acoustic measurements at one or more other azimuths; and
   dividing the difference RMS by the measurement RMS to generate a cement bonding value associated with the axial location.

16. A non-transitory, computer-readable medium having instructions stored thereon that are executable by a computing device to perform operations comprising:
   determining a polar differential signal for each of one or more pairs of azimuthally offset acoustic measurements within a wellbore;
   identifying a reference azimuth based, at least in part, on comparing the polar differential signals to a modeled bonding differential signal within a target response window;

determining differences between an acoustic measurement at the reference azimuth and acoustic measurements at one or more other azimuths; and determining a wellbore material condition based, at least in part, on the determined differences.

17. The computer-readable medium of claim 16, wherein the wellbore material condition is a cement bonding condition, and wherein the instructions include instructions executable by the computing device to perform operations comprising:

generate a bonded response from a bonded acoustic response model and a free pipe response from a free pipe acoustic response model, wherein the bonded acoustic response model and the free pipe acoustic response model are configured using wellbore parameters; and generate the modeled differential signal by subtracting the free pipe response from the bonded response.

18. The computer-readable medium of claim 17, wherein identifying a reference azimuth includes:

comparing at least a portion of the modeled bonding differential signal to a temporally corresponding portion of each of the polar differential signals; and selecting as the reference azimuth, the azimuth at which a closest match is determined between the portion of the modeled bonding differential signal and the temporally corresponding portion of a polar differential signal.

19. The computer-readable medium of claim 18, wherein the portion of the modeled bonding differential signal and the temporally corresponding portion of each of the polar differential signals comprises a cement boundary echo window.

20. The computer-readable medium of claim 16, wherein the instructions include instructions executable by the computing device to perform operations comprising collecting the one or more pairs of azimuthally offset acoustic measurements at an axial location along the wellbore, wherein the wellbore material condition comprises a cement bonding condition, and wherein determining the wellbore material condition based, at least in part, on the determined differences includes:

calculating a difference root mean square (RMS) comprising the RMS of the differences between the acoustic measurement at the reference azimuth and acoustic measurements at one or more other azimuths;

calculating a measurement RMS comprising the RMS of the acoustic measurements at one or more other azimuths; and dividing the difference RMS by the measurement RMS to generate a cement bonding value associated with the axial location.

* * * * *